US006342566B2

(12) United States Patent
Burkhardt et al.

(10) Patent No.: US 6,342,566 B2
(45) Date of Patent: Jan. 29, 2002

(54) PROPYLENE IMPACT COPOLYMERS

(75) Inventors: Terry John Burkhardt, Kingwood; Robert Tan Li, Houston; Aspy Keki Mehta, Humble; Udo M. Stehling; William T. Haygood, Jr., both of Houston; Francis C. Rix, League City, all of TX (US); Dawn C. Wiser, Lake Forest, IL (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/862,667

(22) Filed: May 21, 2001

Related U.S. Application Data

(62) Division of application No. 09/535,357, filed on Mar. 24, 2000.
(60) Provisional application No. 60/181,016, filed on Feb. 8, 2000.

(51) Int. Cl.⁷ ............................ C08L 23/00; C08L 23/04
(52) U.S. Cl. ........................................ 525/191; 525/240
(58) Field of Search .................................. 525/191, 240

(56) References Cited

U.S. PATENT DOCUMENTS

| | | |
|---|---|---|
| 5,118,757 A | 6/1992 | McCullough, Jr. |
| 5,166,268 A | 11/1992 | Ficker |
| 5,250,631 A | 10/1993 | McCullough, Jr. |
| 5,258,464 A | 11/1993 | McCullough, Jr. et al. |
| 5,362,782 A | 11/1994 | McCullough, Jr. et al. |
| 5,382,631 A | 1/1995 | Stehling et al. |
| 5,623,022 A | 4/1997 | Sugano et al. |
| 5,672,668 A | 9/1997 | Winter et al. |
| 5,712,344 A | 1/1998 | McCullough, Jr. et al. |
| 5,747,576 A | 5/1998 | Sobajima et al. |
| 5,770,753 A | 6/1998 | Küber et al. |
| 5,830,821 A | 11/1998 | Rohrmann et al. |
| 5,840,644 A | 11/1998 | Küber et al. |
| 5,840,808 A | 11/1998 | Sugimura et al. |
| 5,854,354 A | 12/1998 | Ueda et al. |
| 5,942,587 A | 8/1999 | Arjunan et al. |
| 5,948,839 A | 9/1999 | Chatterjee |
| 5,990,220 A | 11/1999 | Sobajima et al. |
| 5,990,242 A | 11/1999 | Naga et al. |

FOREIGN PATENT DOCUMENTS

| | | |
|---|---|---|
| EP | 0 629 632 A | 12/1994 |
| EP | 0 641 807 A | 3/1995 |
| EP | 0 657 500 A | 6/1995 |
| EP | 0 962 474 A | 12/1999 |
| WO | WO98/40331 | 9/1998 |
| WO | WO99/12943 | 3/1999 |

OTHER PUBLICATIONS

Journal of Polymer Science: Part A: Polymer Chemistry, vol. 36, 1527–1542 (1998) 1998 John Wiley & Sons, Inc. entitled "Sequence Distributions versus Catalyst Site Behavior of in Situ Blends of Polypropylene and Poly (ethylene–co–propylene)".

*Primary Examiner*—Nathan M. Nutter
(74) *Attorney, Agent, or Firm*—Kevin M. Faulkner; C. Paige Schmidt

(57) ABSTRACT

This invention relates to propylene impact copolymer compositions. In particular, these unique and improved compositions can be produced using conventional, commercial-scale processes.

14 Claims, No Drawings

PROPYLENE IMPACT COPOLYMERS

The present application is a Divisional Application of U.S. Ser. No. 09/535,357, filed on Mar. 24, 2000, which claims priority to Provisional Application U.S. Ser. No. 60/181,016, filed Feb. 8, 2000.

FIELD

This invention relates to propylene impact copolymer compositions. In particular, these unique and improved compositions can be produced using metallocene catalysts in commercial-scale processes.

BACKGROUND

Propylene impact copolymers are commonly used in a variety of applications where strength and impact resistance are desired such as molded and extruded automobile parts, household appliances, luggage and furniture. Propylene homopolymers are often unsuitable for such applications because they are too brittle and have low impact resistance particularly at low temperature, whereas propylene impact copolymers are specifically engineered for applications such as these.

A typical propylene impact copolymer contains two phases or components, a homopolymer component and a copolymer component. These two components are usually produced in a sequential polymerization process wherein the homopolymer produced in a first reactor is transferred to a second reactor where copolymer is produced and incorporated within the matrix of the homopolymer component. The copolymer component has rubbery characteristics and provides the desired impact resistance, whereas the homopolymer component provides overall stiffness.

Many process variables influence the resulting impact copolymer and these have been extensively studied and manipulated to obtain various desired effects. For example U.S. Pat. No. 5,166,268 describes a "cold forming" process for producing propylene impact copolymers where finished articles are fabricated at temperatures below the melting point of the preform material, in this case, the propylene impact copolymer. The patented process uses a propylene impact copolymer comprised of either a homopolymer or crystalline copolymer matrix (first component) and at least ten percent by weight of an "interpolymer" of ethylene and a small amount of propylene (the second component). Adding comonomer to the first component lowers its stiffness. The ethylene/propylene copolymer second component enables the finished, cold-formed article to better maintain its shape.

U.S. Pat. No. 5,258,464 describes propylene impact copolymers with improved resistance to "stress whitening." Stress whitening refers to the appearance of white spots at points of impact or other stress. These otherwise conventional propylene impact copolymers have first and second components characterized by a numerical ratio of the second component intrinsic viscosity to the first component intrinsic viscosity which is near unity.

In U.S. Pat. No. 5,362,782, nucleating agent is added to propylene impact copolymers having a numerical ratio of the intrinsic viscosity of the copolymer rubber phase (second component) to the intrinsic viscosity of the homopolymer phase (first component) which is near unity, and an ethylene content of the copolymer phase in the range of 38% to 60% by weight. These propylene impact copolymers are described as producing articles having good clarity as well as impact strength and resistance to stress whitening. The nucleating agents increase stiffness and impact strength.

U.S. Pat. No. 5,250,631 describes a propylene impact copolymer having a homopolypropylene first component and an ethylene/butene/propylene terpolymer second component. Again, the goal is to obtain high impact strength coupled with resistance to stress whitening.

Propylene impact copolymers are also used to produce films as described in U.S. Pat. No. 5,948,839. The impact copolymer described in this patent contains a conventional first component and 25 to 45 weight percent ethylene/propylene second component having from 55 to 65 weight percent ethylene. This impact copolymer composition has a melt flow of from 7 to 60 dg/min. Such films are used in articles such as diapers.

Recently, efforts have been made to prepare propylene impact copolymers using the newly developed metallocene catalysis technology in order to capitalize on the inherent benefits such catalysts provide. It is well known that homopolymers prepared with such "single-site" catalysts have narrow molecular weight distributions, and low extractables and a variety of other favorable properties associated therewith. Metallocene catalyzed copolymers have narrow composition distributions in addition to narrow molecular weight distribution and low extractables.

Unfortunately, known metallocenes are not able to provide copolymer components with high enough molecular weight under commercially relevant process conditions. The resulting propylene impact copolymers have poor impact strength compared to their conventionally catalyzed counterparts.

U.S. 5,990,242 approaches this problem by using an ethylene/butene (or higher α-olefin) copolymer second component, rather than a propylene copolymer, prepared using a hafnocene type metallocene. Such hafnium metallocenes in general are known for producing relatively higher molecular weight polymers; however, their activities are much lower than the more commonly used zirconocenes. In any event, the second component molecular weights and intrinsic viscosities are lower than desired for good impact strength.

The present inventors have discovered new propylene impact copolymer compositions having the benefits of metallocene catalyzed polymers in addition to properties needed for high impact strength. Importantly, these polymers can be economically produced using commercial-scale processes.

SUMMARY

The present invention provides reactor produced propylene impact copolymer compositions comprising:
  (a) From about 40% to about 95% by weight Component A based on the total weight of the impact copolymer, Component A comprising propylene homopolymer or copolymer wherein the copolymer comprises 10% or less by weight ethylene, butene, hexene or octene comonomer;
  (b) From about 5% to about 60% by weight Component B based on the total weight of the impact copolymer, Component B comprising propylene copolymer wherein the copolymer comprises from about 20% to about 70% by weight ethylene, butene, hexene and/or octene comonomer, and from about 80% to about 30% by weight propylene, wherein Component B:
    (i) has a weight average molecular weight of at least 100,000;
    (ii) a composition distribution of greater than 60%; and
    (iii) an intrinsic viscosity of greater than 1.00 dl/g.

This invention also provides a process for producing propylene impact copolymer in a multiple stage process wherein Component A comprising propylene homopolymer or copolymer wherein the copolymer comprises 10% or less by weight ethylene, butene, hexene or octene comonomer is produced in a primary stage and Component B is produced in a subsequent stage, Component B comprising propylene copolymer wherein the copolymer comprises from about 20% to about 70% by weight ethylene, butene, hexene and/or octene comonomer, and from about 80% to about 30% by weight propylene, wherein at least one of Components A and/or B are polymerized using a metallocene selected from the group consisting of: rac-dimethylsiladiyl (2-iPr,4-phenylindenyl)$_2$zirconium dichloride; rac-dimethylsiladiyl(2-iPr,4-[1-naphthyl]indenyl)$_2$zirconium dichloride; rac-dimethylsiladiyl(2-iPr, 4-[3,5-dimethylphenyl]indenyl)$_2$zirconium dichloride; rac-dimethylsiladiyl(2-iPr, 4-[ortho-methyl-phenyl]indenyl)$_2$ zirconium dichloride; and rac-diphenylsiladiyl(2-methyl-4-[1-naphthyl]indenyl)$_2$zirconium dichloride.

DESCRIPTION

The propylene impact copolymers ("ICPs") of this invention comprise at least two major components, Component A and Component B. Component A is preferably an isotactic propylene homopolymer, though small amounts of a comonomer may be used to obtain particular properties. Typically such copolymers of Component A contain 10% by weight or less, preferably less than 6% by weight or less, comonomer such as ethylene, butene, hexene or octene. Most preferably less than 4% by weight ethylene is used. The end result is usually a product with lower stiffness but with some gain in impact strength compared to homopolymer Component A.

As used herein Component A refers generally to the xylene insoluble portion of the ICP composition, and Component B refers generally to the xylene soluble portion. Where the xylene soluble portion clearly has both a high molecular weight component and a low molecular weight component, we have found that the low molecular weight component is attributable to amorphous, low molecular weight propylene homopolymer. Therefore, Component B in such circumstances refers only the high molecular weight portion.

Component A preferably has a narrow molecular weight distribution Mw/Mn ("MWD"), i.e., lower than 4.0, preferably lower than 3.5, more preferably lower than 3.0, and most preferably 2.5 or lower. These molecular weight distributions are obtained in the absence of visbreaking using peroxide or other post reactor treatment designed to reduce molecular weight. Component A preferably has a weight average molecular weight (Mw as determined by GPC) of at least 100,000, preferably at least 200,000 and a melting point (Mp) of at least 145° C., preferably at least 150° C., more preferably at least 152° C., and most preferably at least 155° C.

Another important feature of ICPs is the amount of amorphous polypropylene they contain. The ICPs of this invention are characterized as having low amorphous polypropylene, preferably less than 3% by weight, more preferably less than 2% by weight, even more preferably less than 1% by weight and most preferably there is no measurable amorphous polypropylene.

Component B is most preferably a copolymer consisting essentially of propylene and ethylene although other propylene copolymers, ethylene copolymers or terpolymers may be suitable depending on the particular product properties desired. For example, propylene/butene, hexene or octene copolymers, and ethylene/butene, hexene or octene copolymers may be used, and propylene/ethylene/hexene-1 terpolymers may be used. In a preferred embodiment though, Component B is a copolymer comprising at least 40% by weight propylene, more preferably from about 80% by weight to about 30% by weight propylene, even more preferably from about 70% by weight to about 35% by weight propylene. The comonomer content of Component B is preferably in the range of from about 20% to about 70% by weight comonomer, more preferably from about 30% to about 65% by weight comonomer, even more preferably from about 35% to about 60% by weight comonomer. Most preferably Component B consists essentially of propylene and from about 20% to about 70% ethylene, more preferably from about 30% to about 65% ethylene, and most preferably from about 35% to about 60% ethylene.

For other Component B copolymers, the comonomer contents will need to be adjusted depending on the specific properties desired. For example, for ethylene/hexene copolymers, Component B should contain at least 17% by weight hexene and at least 83% by weight ethylene.

Component B, preferably has a narrow molecular weight distribution Mw/Mn ("MWD"), i.e., lower than 5.0, preferably lower than 4.0, more preferably lower than 3.5, even more preferably lower than 3.0 and most preferably 2.5 or lower. These molecular weight distributions should be obtained in the absence of visbreaking or peroxide or other post reactor treatment designed to reduce molecular weight. Component B preferably has a weight average molecular weight (Mw as determined by GPC) of at least 100,000, preferably at least 150,000, and most preferably at least 200,000.

Component B preferably has an intrinsic viscosity greater than 1.00 dl/g, more preferably greater than 1.50 dl/g and most preferably greater than 2.00 dl/g. The term "intrinsic viscosity" or "IV" is used conventionally herein to mean the viscosity of a solution of polymer such as Component B in a given solvent at a given temperature, when the polymer composition is at infinite dilution. According to the ASTM standard test method D 1601-78, IV measurement involves a standard capillary viscosity measuring device, in which the viscosity of a series of concentrations of the polymer in the solvent at the given temperature are determined. For Component B, decalin is a suitable solvent and a typical temperature is 135° C. From the values of the viscosity of solutions of varying concentrations, the "value" at infinite dilution can be determined by extrapolation.

Component B preferably has a composition distribution (CD) of greater than 60%, more preferably greater than 65%, even more preferably greater than 70%, even more preferably greater than 75%, still more preferably greater than 80%, and most preferably greater than 85%. CD defines the compositional variation among polymer chains in terms of ethylene (or other comonomer) content of the copolymer as a whole. The measurement of CD is described in detail U.S. Pat. No. 5,191,042 which is hereby fully incorporated by reference. CD is defined herein as the weight percent of the copolymer molecules having a comonomer content within 50% of the median total molar comonomer content.

As described in U.S. Pat. No. 5,191,042, CD is determined by first determining the mean ethylene (or other comonomer) content of the copolymer by a suitable test such as ASTM D-3900. Next, the copolymer sample is dissolved in solvent such as hexane and a number of fractions of differing composition are precipitated by the addition of incremental amounts of a liquid such as isopropanol in which the copolymer is insoluble. Generally from about 4 to 6 fractions are precipitated in this way and the weight and ethylene (or other comonomer) content of each fraction are determined after removing the solvent. From the weight of each fraction and its ethylene content, a plot is prepared of weight percent composition vs. cumulative weight percent of polymer, and a smooth curve is drawn through the points.

Component B of the ICPs preferably has low crystallinity, preferably less than 10% by weight of a crystalline portion, more preferably less than 5% by weight of a crystalline portion. Where there is a crystalline portion of Component B, its composition is preferably the same as or at least similar to (within 15% by weight) the remainder of Component B in terms of overall comonomer weight percent.

The ICPs of this invention are "reactor produced" meaning Components A and B are not physically or mechanically blended together. Rather, they are interpolymerized in at least one reactor. The final ICP as obtained from the reactor or reactors, however, can be blended with various other components including other polymers.

The preferred melt flow rate ("MFR") of these ICPs depends on the desired end use but is typically in the range of from about 0.2 dg/min to about 200 dg/min, more preferably from about 5 dg/min to about 100 dg/min. Significantly, high MFRs, i.e., higher than 50 dg/min are obtainable. MFR is determined by a conventional procedure such as ASTM-1238 Cond. L. The ICP preferably has a melting point of at least 145° C., preferably at least 150° C., more preferably at least 152° C., and most preferably at least 155° C.

The ICPs comprise from about 40% to about 95% by weight Component A and from about 5% to about 60% by weight Component B, preferably from about 50% to about 95% by weight Component A and from about 5% to about 50% Component B, even more preferably from about 60% to about 90% by weight Component A and from about 10% to about 40% by weight Component B. In the most preferred embodiment, the ICP consists essentially of Components A and B. The overall comonomer (preferably ethylene) content of the total ICP is preferably in the range of from about 2% to about 30% by weight, preferably from about 5% to about 25% by weight, even more preferably from about 5% to about 20% by weight, still more preferably from about 5% to about 15% by weight comonomer.

A variety of additives may be incorporated into the ICP for various purposes. Such additives include, for example, stabilizers, antioxidants, fillers, colorants, nucleating agents and mold release agents.

The ICP compositions of this invention may be prepared by conventional polymerization processes such as a two-step process. It is conceivable, although currently impractical, to commercially produce ICPs in a single reactor. Each step may be independently carried out in either the gas or liquid slurry phase. For example the first step may be conducted in the gas phase and the second in liquid slurry or vice versa. Alternatively, each phase may be the same. Preferably the ICPs of this invention are produced in multiple reactors, preferably two or three, operated in series, Component B is preferably polymerized in a second, gas phase reactor. Component A is preferably polymerized first, in a liquid slurry or solution polymerization process.

In an alternative embodiment, Component A is made in at least two reactors in order to obtain fractions with varying melt flow rate. This has been found to improve the processability of the ICP.

As used herein "stage" is defined as that portion of a polymerization process during which one component of the ICP, Component A or Component B, is produced. One or multiple reactors may be used during each stage.

Hydrogen may be added to one or both reactors to control molecular weight, IV and MFR. The use of hydrogen for such purposes is well known to those skilled in the art.

Preferably a metallocene catalyst system is used to produce the ICP compositions of this invention. To date it appears that the most suitable metallocenes are those in the generic class of bridged, substituted bis(cyclopentadienyl) metallocenes, specifically bridged, substituted bis(indenyl) metallocenes known to produce high molecular weight, high melting, highly isotactic propylene polymers. Generally speaking, those of the generic class disclosed in U.S. Pat. No. 5,770,753 (fully incorporated herein by reference) should be suitable, however, it has been found that the exact polymer obtained is highly dependent on the metallocene's specific substitution pattern.

We have found that the following racemic metallocenes are most suitable for preparing the ICP compositions of this invention: rac-dimethylsiladiyl(2-iPr,4-phenylindenyl)$_2$ zirconium dichloride; rac-dimethylsiladiyl(2-iPr,4-[1-naphthyl]indenyl)$_2$zirconium dichloride; rac-dimethylsiladiyl(2-iPr, 4-[3,5-dimethylphenyl]indenyl)$_2$ zirconium dichloride; rac-dimethylsiladiyl(2-iPr, 4-[ortho-methyl-phenyl]indenyl)$_2$zirconium dichloride; and rac-diphenylsiladiyl(2-methyl-4-[1-naphthyl]indenyl)$_2$ zirconium dichloride. It will be immediately apparent to those skilled in the art that certain modifications to these metallocene species are not likely to result in significantly modified ICP composition though activity or ease of synthesis may be impacted. While not wishing to be bound by theory, it is believed that the critical feature of these specific metallocenes is their substitution pattern on the base indenyl group. Thus, it is believed that changing the bridge, for example substituting carbon for silicon, or changing the metal to hafnium or titanium, or changing the metal dichloride to some other dihalide or dimethyl, will not significantly change the ICP compositions of this invention. On the other hand, substituting a group at any position on the indenyl for another or adding one or more groups or substitutents is likely to result in a significantly different composition which may or may not be an ICP of this invention.

Metallocenes are generally used in combination with some form of activator in order to create an active catalyst system. The term "activator" is defined herein to be any compound or component, or combination of compounds or components, capable of enhancing the ability of one or more metallocenes to polymerize olefins. Alkylalumoxanes such as methylalumoxane (MAO) are commonly used as metallocene activators. Generally alkylalumoxanes contain 5 to 40 of the repeating units:

R(AlRO )xAlR$_2$ for linear species and (AlRO )x for cyclic species where R is a $C_1$–$C_8$ alkyl including mixed alkyls. Compounds in which R is methyl are particularly preferred. Alumoxane solutions, particularly methylalumoxane solutions, may be obtained from commercial vendors as solutions having various concentrations. There are a variety of methods for preparing alumoxane, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,103,031 and EP-A-0 561 476, EP-B1-0 279 586, EP-A-0 594-218 and WO 94/10180, each fully incorporated herein by reference.

Ionizing activators may also be used to activate metallocenes. These activators are neutral or ionic, or are compounds such as tri(n-butyl)ammonium tetrakis (pentafluorophenyl)borate, which ionize the neutral metallocene compound. Such ionizing compounds may contain an active proton, or some other cation associated with, but not coordinated or only loosely coordinated to, the remaining ion of the ionizing compound. Combinations of activators may also be used, for example, alumoxane and ionizing activator combination, see for example, WO 94/07928.

Descriptions of ionic catalysts for coordination polymerization comprised of metallocene cations activated by non-coordinating anions appear in the early work in EP-A-0 277 003, EP-A-0 277 004 and U.S. Pat. No. 5,198,401 and WO-A-92/00333 (incorporated herein by reference). These teach desirable methods of preparation wherein metallocenes (bisCp and monoCp) are protonated by an anion precursor such that an alkyl/hydride group is abstracted from a transition metal to make it both cationic and charge-balanced by the non-coordinating anion. Suitable ionic salts include tetrakis-substituted borate or aluminum salts having fluorided aryl-constituents such as phenyl, biphenyl and napthyl.

The term "noncoordinating anion" (NCA) means an anion which either does not coordinate to said cation or which is only weakly coordinated to said cation thereby remaining sufficiently labile to be displaced by a neutral Lewis base. "Compatible" noncoordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Particularly useful non-coordinating anions are those which are compatible, stabilize the metallocene cation in the sense of balancing its ionic charge in a +1 state, yet retain sufficient lability to permit displacement by an ethylenically or acetylenically unsaturated monomer during polymerization.

The use of ionizing ionic compounds not containing an active proton but capable of producing both the active metallocene cation and a noncoordinating anion is also known. See, for example, EP-A-0 426 637 and EP-A-0 573 403 (incorporated herein by reference). An additional method of making the ionic catalysts uses ionizing anion precursors which are initially neutral Lewis acids but form the cation and anion upon ionizing reaction with the metallocene compounds, for example the use of tris (pentafluorophenyl) borane. See EP-A-0 520 732 (incorporated herein by reference). Ionic catalysts for addition polymerization can also be prepared by oxidation of the metal centers of transition metal compounds by anion precursors containing metallic oxidizing groups along with the anion groups, see EP-A-0 495 375 (incorporated herein by reference).

Where the metal ligands include halogen moieties (for example, biscyclopentadienyl zirconium dichloride) which are not capable of ionizing abstraction under standard conditions, they can be converted via known alkylation reactions with organometallic compounds such as lithium or aluminum hydrides or alkyls, alkylalumoxanes, Grignard reagents, etc. See EP-A-0 500 944 and EP-A1-0 570 982 (incorporated herein by reference) for in situ processes describing the reaction of alkyl aluminum compounds with dihalo-substituted metallocene compounds prior to or with the addition of activating anionic compounds.

Methods for supporting ionic catalysts comprising metallocene cations and NCA are described in U.S. Pat. No. 5,643,847, U.S. patent application Ser. No. 09184358, filed Nov. 2, 1998 and U.S. patent application Ser. No. 09184389, filed Nov. 2, 1998 (all fully incorporated herein by reference).

When the activator for the metallocene supported catalyst composition is a NCA, preferably the NCA is first added to the support composition followed by the addition of the metallocene catalyst. When the activator is MAO, preferably the MAO and metallocene catalyst are dissolved together in solution. The support is then contacted with the MAO/metallocene catalyst solution. Other methods and order of addition will be apparent to those skilled in the art.

The catalyst systems used to prepare the compositions of this invention are preferably supported using a porous particulate material, such as for example, talc, inorganic oxides, inorganic chlorides and resinous materials such as polyolefin or polymeric compounds.

Preferably, the support materials are porous inorganic oxide materials, which include those from the Periodic Table of Elements of Groups 2, 3, 4, 5, 13 or 14 metal oxides. Silica, alumina, silica-alumina, and mixtures thereof are particularly preferable. Other inorganic oxides that may be employed either alone or in combination with the silica, alumina or silica-alumina are magnesia, titania, zirconia, and the like.

Preferably the support material is porous silica which has a surface area in the range of from 10 to 700 m$^2$/g, a total pore volume in the range of from 0.1 to 4.0 cc/g and an average particle size in the range of from 10 to 500 µm. More preferably, the surface area is in the range of from 50 to 500 m$^2$/g, the pore volume is in the range of from 0.5 to 3.5 cc/g and the average particle size is in the range of from 20 to 200 µm. Most desirably the surface area is in the range of from 100 to 400 m$^2$/g, the pore volume is in the range of from 0.8 to 3.0 cc/g and the average particle size is in the range of from 30 to 100 µm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

The metallocenes, activator and support material may be combined in any number of ways. Suitable support techniques are described in U.S. Pat. Nos. 4,808,561 and 4,701,432 (each fully incorporated herein by reference). Preferably the metallocenes and activator are combined and their reaction product supported on the porous support material as described in U. S. Pat. No. 5,240,894 and WO 94/ 28034, WO 96/00243, and WO 96/00245 (each fully incorporated herein by reference). Alternatively, the metallocenes may be preactivated separately and then combined with the support material either separately or together. If the metallocenes are separately supported, then preferably, they are dried then combined as a powder before use in polymerization.

Regardless of whether the metallocenes and their activator are separately precontacted or whether the metallocenes and activator are combined at once, the total volume of reaction solution applied to porous support is desirably less than 4 times the total pore volume of the porous support, more desirably less than 3 times the total pore volume of the porous support and even more desirably in the range of from more than 1 to less than 2.5 times the total pore volume of the porous support. Procedures for measuring the total pore volume of porous support are well known in the art. One such method is described in Volume 1, Experimental Methods in Catalyst Research, Academic Press, 1968, pages 67–96.

Methods of supporting ionic catalysts comprising metallocene cations and noncoordinating anions are described in WO 91/09882, WO 94/03506, WO 96/04319 and in co-pending U.S. Ser. No. 08/248,284, filed Aug. 3 1994 (incorporated herein by reference). The methods generally comprise either physical adsorption on traditional polymeric or inorganic supports that have been largely dehydrated and dehydroxylated, or using neutral anion precursors that are sufficiently strong Lewis acids to activate retained hydroxy groups in silica containing inorganic oxide supports such that the Lewis acid becomes covalently bound and the hydrogen of the hydroxy group is available to protonate the metallocene compounds.

The supported catalyst system may be used directly in polymerization or the catalyst system may be prepolymerized using methods well known in the art. For details regarding prepolymerization, see U.S. Pat. Nos. 4,923,833 and 4,921,825, EP 0 279 863 and EP 0 354 893 each of which is fully incorporated herein by reference.

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

EXAMPLES

All air sensitive experiments are carried out in nitrogen purged dry boxes. All solvents were purchased from commercial sources. 4-Chloro-2-isopropylindene was purchased from commercial sources. Aluminum alkyls were purchased as hydrocarbon solutions from commercial sources. The commercial methylalumoxane ("MAO") was purchased from Albemarle as a 30 wt % solution in toluene.

METALLOCENE SYNTHESIS

Metallocene A: racemic dimethylsiladiyl(2-isopropyl-4-phenylindenyl)$_2$ zirconium dichloride was obtained from commercial sources and used as received.

Metallocene B: racemic dimethylsiladiyl(2-isopropyl-4-[1-naphthyl]indenyl)$_2$ zirconium dichloride was obtained from commercial sources and used as received.

Metallocene C: racemic dimethylsiladiyl(2-isopropyl-4-[2-methyl-phenyl]indenyl)$_2$ zirconium dichloride was prepared as follows:

4-(2-methylphenyl)-2-isopropylindene

4–Chloro-2-isopropylindene (9.8 g, 51 mmol) and NiCl$_2$(PPh$_3$)$_2$ (1.8 g, 2.8 mmol) are dissolved in 150 mL of Et$_2$O. 2-Methylphenylmagnesium bromide (51 mmol) as an Et$_2$0 solution was added to the solution and the reaction was stirred overnight at room temperature. After overnight stirring, the reaction was slowly quenched with H$_2$O to neutralize unreacted Grignard. The solution was subsequently treated with 100 mL of 10% HCl(aq) and neutralized with saturated sodium bicarbonate aqueous solution. The organic layer was dried with magnesium sulfate and the solvent was removed by rotary evaporation. The remaining residue was loaded onto a silica gel column and eluted with hexane. Yield was 6.6 g (52%).

Lithium 4-(2-methylphenyl)-2-isopropylindenide 4-(2-methylphenyl)-2-isopropylindene (6.6 g, 26.5 mmol) was dissolved in 80 mL of pentane. To this solution was added 10.6 mL of n-BuLi (2.5M in hexane) and the reaction was allowed to stir 4 hours at room temperature. A white solid precipitates from solution and was collected by frit filtration and washed with additional pentane. Yield was 5.8 g (88%).

Dimethylsiladiylbis[4-(2-methylphenyl)-2-isopropylindene]

SiMe$_2$Cl$_2$ (0.88 g, 6.8 mmol) was dissolved in 60 mL of THF. While stirring, lithium 4-(2-methylphenyl)-2-isopropylindenide (3.5 g, 13.7 mmol) was added as a dry powder and the contents are allowed to stir overnight at room temperature. The solvent was removed in vacuo and the residue was taken up in pentane and filtered to remove LiCl salts. The pentane was removed in vacuo to yield a flaky, white solid (3.0 g).

Dimethylsiladiylbis[4-(2-methylphenyl)-2-isopropylindenyl]ZrCl$_2$

Dimethylsiladiylbis[4-(2-methylphenyl)-2-isopropylindene] (3.0 g, 5.4 mmol) was dissolved in 60 mL of Et$_2$O. While stirring, 4.5 mL of n-BuLi (2.5M in hexane) was added and allowed to stir at room temperature for 2 hours. After this time, the solution was cooled to −35° C. and ZrCl$_4$ (1.25 g, 5.4 mmol) was added and allowed to stir at room temperature for 3 hours. The solvent was then removed in vacuo and the residue was taken up in a mixture of methylene chloride and pentane and filtered to remove LiCl salts. The filtrate was then concentrated and chilled to −35° C. to induce crystallization. 0.26 g (6.7%) of pure racemic compound was obtained.

Metallocene D: racemic dimethylsiladiyl(2-isopropyl-4-[3,5-dimethylphenyl]indenyl)$_2$ zirconium dichloride was prepared as follows:

4-(3,5-dimethylphenyl)-2-isopropylindene

4-Chloro-2-isopropylindene (10.4 g, 54 mmol) and NiCl$_2$(PPh$_3$)$_2$ (1.8 g, 2.8 mmol) are dissolved in 150 mL of Et$_2$O. 3,5-dimethylphenylmagnesium bromide (54 mmol) as an Et$_2$O solution was added under vigorous stirring and the reaction was stirred overnight at room temperature. After overnight stirring, the reaction was slowly quenched with H$_2$O to neutralize unreacted Grignard. The solution was subsequently treated with 100 mL of 10% HCl (aq) and neutralized with saturated sodium bicarbonate aqueous solution. The organic layer was dried with magnesium sulfate, and the solvent was removed by rotary evaporation. The remaining residue was loaded onto a silica gel column and eluted with hexane. Yield was 5.5 g (39%).

Lithium 4-(3,5-dimethylphenyl)-2-isopropylindenide 4-(3,5-Dimethylphenyl)-2-isopropylindene (5.5 g, 21 mmol) was dissolved in 80 mL of pentane. To this solution was added 8.3 mL of n-BuLi (2.5M in hexane) and the reaction was allowed to stir 4 hours at room temperature. A white solid precipitates from solution and was collected by frit filtration and washed with additional pentane. Yield was 3.28 g (60%).

Dimethylsiladiylbis[4-(3,5-dimethylphenyl)-2-isopropylindene]

SiMe$_2$Cl$_2$ (0.69 g, 5.4 mmol) was dissolved in 80 mL of THF. While stirring, lithium 4-(3,5-methylphenyl)-2-isopropylindenide (2.9 g, 10.8 mmol) was added as a dry powder and the contents are allowed to stir overnight at room temperature. The solvent was removed in vacuo and the residue was taken up in pentane and filtered to remove LiCl salts. The pentane was removed in vacuo to yield a flaky, white solid (2.1 g, 67%)

Dimethylsiladiylbis[4-(3,5-dimethylphenyl)-2-isopropylindenyl]ZrCl$_2$

Dimethylsiladiylbis[4-(3,5-dimethylphenyl)-2-isopropylindene] (2.1 g, 3.6 mmol) was dissolved in 60 mL of Et$_2$O. While stirring, 2.9 mL of n-BuLi (2.5M in hexane) was added and allowed to stir at room temperature for 2 hours. After this time, the solution was cooled to −35° C. and ZrCl$_4$ (0.83 g, 3.6 mmol) was added and allowed to stir at room temperature for 3 hours. The solvent was then removed in vacuo and the residue was taken up in toluene and filtered to remove LiCl salts. The filtrate was then concentrated and chilled to −35° C. to induce crystallization. 0.24 g (6.0%) of pure racemic compound was obtained.

Metallocene E: racemic diphenylsiladiyl(2-methyl-4-[1-naphthyl]indenyl)$_2$ zirconium dichloride was prepared as follows.

Ph$_2$Si(2-Methyl-4-[1-napthyl]indene)$_2$

2-Methyl-4-[1-napthyl]indenyl lithium (5.5 g, 21 mmol) was added to a solution of Ph$_2$Si(OSO$_2$CF$_3$)$_2$ (4.8 g, 10 mmol) and diethyl ether (50 mL). The mixture was stirred overnight then the product was isolated by filtration, washed with diethyl ether (4×50 mL) then dried in vacuo. Yield 4.71 g, 68%.

The method described above reacting Ph$_2$Si(OSO$_2$CF$_3$)$_2$ with 2-Methyl-4-[1-napthyl]indenyl lithium to form the ligand system with a Ph$_2$Si bridge is a general one. A wide variety of cyclopentadienyl or indenyl metal salts can be reacted with Ph$_2$Si(OSO$_2$CF$_3$)$_2$ when Ph$_2$Si(Cl)$_2$ is unreactive or slow with the cyclopentadienyl or indenyl metal salt reagent.

Ph$_2$Si(2-Methyl-4-[1-napthyl]indenyl SnMe$_3$)$_2$

A slurry of Ph$_2$Si(2-Methyl-4-[1-napthyl]indenyl lithium)$_2$ was prepared from addition of a 2.0 M solution of n-Butyl lithium and pentane (1.5 mL, 3.0 mmol) to a mixture of Ph$_2$Si(2-Methyl, 4-napthyl indene)$_2$ (1.0 g, 1.44 mmol) and diethyl ether (20 mL). After stirring for two hours, trimethyl tin chloride (0.6 g, 3.0 mmol) was added. The color changed instantly from an intense to light yellow. The ether was removed and the product extracted with pentane (3×20 mL). Removal of solvent yielded product. Yield 0.88 g, 60%.

Racemic-Ph$_2$Si(2-Methyl-4-[1-napthyl]indenyl)$_2$ZrCl$_2$

A 100 mL flask was charged with ZrCl$_4$ (180 mg, 0.77 mmol), toluene (20 mL) then Ph$_2$Si(2-Methyl-4-[1-napthyl]indenyl SnMe$_3$)$_2$ (815 mg, 0.8 mmol). The mixture was stirred overnight then heated in vacuo at 90° C. for 48 h. The orange powder was taken up in toluene (5 mL) then filtered through a 0.45 μm filter. Diethyl ether (2–3 mL) was added to the toluene solution and the solution cooled to −30° C. After prolonged cooling crystals were isolated then washed with cold toluene (3×1 mL) then pentane (3×5 mL). After further washing with toluene (3×1 mL) and hexane (3×5 mL) the sample was dried to obtain product. Yield 17 mg, 2.6%.

Comparison Metallocene 1: racemic dimethylsiladiyl(2-methyl-4-phenylindenyl)$_2$ zirconium dichloride was obtained from commercial sources and used as received.

Comparison Metallocene 2: racemic dimethylsiladiyl(2-methyl-4-[1-naphthyl]indenyl)$_2$ zirconium dichloride was obtained from commercial sources and used as received.

Comparison Metallocene 3: racemic dimethylsiladiyl(2-methyl-4-phenylindenyl)$_2$ zirconium dichloride was obtained from commercial sources and used as received.

Comparison Metallocene 4: racemic dimethylsiladiyl(2-ethyl-4-phenylindenyl)$_2$ zirconium dichloride was obtained from commercial sources and used as received.

SUPPORTED CATALYST SYSTEM SYNTHESIS

Supported Metallocene Catalyst System A

In a 100 mL round bottom flask dimethylsiladiyl(2-iPr-4-phenyl indenyl)$_2$ zirconium dichloride (A, 0.060 g) was added to the MAO-toluene solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twenty minutes. The supported catalyst was recovered as a reddish purple, free flowing solid (5.71 g).

Supported Metallocene Catalyst System B

In a 100 mL round bottom dimethylsiladiyl(2-isopropyl-4-[1-naphthyl]indenyl)$_2$ zirconium dichloride (B, 0.069 g) was added to the MAO-toluene solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for thirty minutes, then dried at 40° C. for two minutes under vacuum on a rotary evaporator until the liquid evaporated and then the solid was dried a total of about 2 hours and twenty minutes. The supported catalyst was recovered as a light purple, free flowing solid (5.4 g).

Supported Metallocene Catalyst System C

In a 100 mL round bottom dimethylsiladiyl(2-isopropyl-4-[2-methyl-phenyl]indenyl)$_2$ zirconium dichloride (C, 0.069 g) was added to the MAO-toluene solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for thirty minutes then dried at 40° C. for two minutes under vacuum on a rotary evaporator until the liquid evaporated and then the solid was further dried a total of about 2 hours and twenty minutes. The supported catalyst was recovered as a light purple, free flowing solid (5.4 g).

Supported Metallocene Catalyst System D

In a 100 mL round bottom dimethylsiladiyl(2-isopropyl-4-[3,5-dimethylphenyl]indenyl)$_2$ zirconium dichloride (D, 0066 g) was added to the MAO-toluene solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated and then the solid was further dried a total of about 2 hours and twenty minutes. The supported catalyst was recovered as a purple, free flowing solid (5.11 g).

Supported Metallocene Catalyst System E

In a 100 mL round bottom diphenylsiladiyl(2-methyl-4-[1-naphthyl]indenyl)$_2$ zirconium dichloride (E, 0.017 g) was added to the MAO-toluene solution (1.52 g) and stirred twenty minutes. This was filtered through a medium glass frit funnel and washed with toluene (3.2 mL). To the combined filtrates was added dehydrated silica (4.0 g, Davison 948 Regular, 600° C. dehydration). This slurry was stirred for twenty minutes, then dried at 40° C. for two minutes under vacuum on a rotary evaporator until the liquid evaporated and then the solid was further dried a total of about 2 hours and twenty minutes. The supported catalyst was recovered as an orange, free flowing solid (1.06 g).

Supported Metallocene Catalyst System F

In a 100 mL round bottom flask dimethylsiladiyl(2-iPr-4-phenylindenyl)$_2$ zirconium dichloride (F, 0.065 g) was added to the MAO-toluene solution (5.1 g, 5.35 mL) and stirred fifteen minutes. This was filtered through a medium glass frit funnel and washed with toluene (11 mL). To the combined filtrates was added dehydrated silica (4.0 g, Davison 948 Regular, 600° C. dehydration). Toluene (2 mL) was added to this slurry, stirred for twenty minutes, dried at 40° C. for ten minutes under vacuum on a rotary evaporator until the liquid evaporated, and then the solid was further dried a total of about two hours and twenty three minutes. The supported catalyst was recovered as a light purple, free flowing solid (5.58 g).

Supported Metallocene Catalyst System G

In a 100 mL round bottom flask dimethylsiladiyl(2-iPr-4-phenylindenyl)$_2$ zirconium dichloride (G, 0.065 g) was added to the MAO-toluene solution (5.1 g, 5.4 mL) and stirred fifty minutes. This was filtered through a medium glass frit funnel and washed with toluene (13 mL). To the combined filtrates was added dehydrated silica (4.0 g, Davison 948 Regular, 600° C. dehydration). This slurry was stirred for twenty minutes, dried at 40° C. for ten minutes under vacuum on a rotary evaporator until the liquid evaporated and then the solid was further dried a total of about 3 hours. The supported catalyst was recovered as a purple, free flowing solid (5.45 g).

Supported Comparison Metallocene Catalyst System 1

In a 100 mL round bottom racemic dimethylsiladiyl(2-methyl-4-phenylindenyl)$_2$ zirconium dichloride (Comparison metallocene 1, 0.055 g) was added to the MAO-toluene solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated and then the solid was further dried a total of about 2 hours and twenty two minutes. The supported catalyst was recovered as a light orange, free flowing solid (5.63 g).

Supported Comparison Metallocene Catalyst System 2

In a 100 mL round bottom racemic dimethylsiladiyl(2-methyl-4-[1-naphthyl]indenyl)$_2$ zirconium dichloride (Comparison metallocene 2, 0.064 g) was added to the MAO-toluene solution (6.74 g, 7.2 mL) and stirred twenty minutes. This was filtered through a medium glass frit funnel and washed with toluene (14 mL). To the combined filtrates was added dehydrated silica (4.0 g, Davison 948 Regular, 600° C. dehydration). This slurry was stirred for twenty minutes then dried at 40° C. for two minutes under vacuum on a rotary evaporator until the liquid evaporated and then the solid was further dried a total of about 2 hours. The supported catalyst was recovered as an orange, free flowing solid (4.72 g).

Supported Comparison Metallocene Catalyst System 3

In a two gallon mixer racemic dimethylsiladiyl(2-methyl-4-phenylindenyl)$_2$ zirconium dichloride (Comparison metallocene 3, 13.0 g) was dissolved in a MAO solution (300 mL). This was added to a MAO solution (800 mL diluted with 1600 mL toluene) and an additional 150 mL of toluene was added. This was mixed one hour. One half of this solution was added to dehydrated silica (802.2 g, Davison 948 Regular, 600° C. dehydration) and stirred five minutes. The remaining solution was then added and stirred twenty minutes. Additional toluene was added (450 mL). This slurry was stirred for twenty minutes then dried at 46° C. for 11.5 hours under nitrogen flow. The supported catalyst was recovered as an orange, free flowing solid (1092.2 g) which was passed through a 25 mesh screen.

Supported Comparison Metallocene Catalyst System 4

In a 100 mL round bottom racemic dimethylsiladiyl(2-ethyl-4-phenylindenyl)$_2$ zirconium dichloride (Comparison metallocene 4, 0.065 g) was added to the MAO-toluene solution (5.1 g, 5.5 mL) and stirred fifteen minutes. This was filtered through a medium glass frit funnel and washed with toluene (11 mL). To the combined filtrates was added dehydrated silica (4.0 g, Davison 948 Regular, 600° C. dehydration). After one addition mL toluene was added this slurry was stirred for twenty minutes then dried at 40° C. under vacuum on a rotary evaporator until the liquid evaporated and then the solid was further dried a total of 2 hours and 23 minutes. The supported catalyst was recovered as a pink, free flowing solid (5.56 g).

POLYMERIZATIONS

Isotactic Polypropylene Homopolymer

The polymerization procedure for producing homopolymers with the supported catalysts was as follows. In a clean, dry two liter autoclave which had been flushed with propylene vapor, TEAL scavenger (0.3 mL, 1.5M) was added. Hydrogen gas was added at this point. The reactor was closed and filled with 800 mL liquid propylene. After heating the reactor to 70° C., the catalyst was added by washing in with propylene (200 mL). After the indicated time, typically one hour, the reactor was cooled, and the excess propylene vented. The polymer was removed and dried. Results are shown in Tables 1A and 2A.

Impact Copolymers (ICP)

The polymerization procedure for producing ICP with the supported catalysts was as follows. In a clean, dry two liter autoclave which had been flushed with propylene vapor, TEAL scavenger (0.3 mL, 1.5M) was added. Hydrogen gas was added at this point. The reactor was closed and filled with 800 mL liquid propylene. After heating the reactor to 70° C., the catalyst was added by washing in with propylene (200 mL). After the indicated time, typically one hour, the reactor was vented to about 170 psig pressure and then an ethylene/propylene gas mixture was passed through the reactor at the rates indicated while maintaining 200 psig. At the end of the gas phase stage, typically 90 to 150 minutes, the reactor was vented and cooled under N2. The granular ICP polymer was removed and dried. Results are shown in Tables 1A and 2A.

POLYMER ANALYSIS

Results are shown in Tables 1B, 2B and 3–8. Molecular weight determinations were made by gel permeation chromatography (GPC) according to the following technique. Molecular weights and molecular weight distributions were measured using a Waters 150° C. gel permeation chromatography equipped with Shodex (Showa Denko) AT-80 M/S columns and a differential refractive index (DRI) detector operating at 145° C. with 1,2,4-trichlorobenzene as the mobile phase at a 1.0 mL/min. flow rate. The sample injection volume was 300 microliters. The columns were calibrated using narrow polystyrene standards to generate a universal calibration curve. The polypropylene calibration curve was established using $k=8.33\times10^{-5}$ and $a=0.800$ as the Mark-Houwink coefficients. The numerical analyses were performed using Waters "Millennium" software.

DSC melting points were determined on commercial DSC instruments and are reported as the second melting point. The polymer sample was heated to 230.0° C. for ten minutes and then cooled from 230° C. to 50° C. at 10° C./minute. The sample is held at 50° C. for five minutes. The second melt is then recorded as the sample is heated from 50° C. to 200° C. at a rate of 10° C./minute. The peak temperature is recorded as the second melting point.

ICP POLYMER EXTRACTION METHOD

The ICP polymer was dissolved in hot xylene and then allowed to cool overnight. After filtration the insolubes are dried. The xylene soluble portion was evaporated and the soluble material recovered. The IV of the recovered soluble material was measured in decalin at 135° C. by using know methods and instruments such as a Schott A VSPro Viscosity Automatic Sampler.

At very high ICP MFR this method can extract some low molecular weight isotactic PP and thus lower the observed IV.

ICP POLYMER FRACTIONATION METHOD

The ICP samples were sent to Polyhedron Laboratories, Inc. to be fractionated and analyzed by GPC. A general description of the procedure is found in the reference J. C. Randall, J. Poly. Sci.: Part A Polymer Chemistry, Vol. 36, 1527–1542 (1998).

The impact copolymers of this invention display improved impact properties as measured by the room temperature notched Izod values at similar Flexural Modulus. This can be seen by examining Table 8. For example, the ICP from inventive run 43 with inventive metallocene F has a Flexural Modulus of 151.8K with a Notched Izod of 1.57 value, and the ICP from inventive run 50 with inventive metallocene G has a Flexural Modulus of 158.3K with a Notched Izod of 1.7 value. The comparative examples shown in runs 46, 47 and 48 where the second values for each are 158.6K, 155.8K and 155.7K with an inferior notched Izods of 1.25, 0.81 and 0.74 values. Thus both inventive runs 43 and 50 have better impact strength as measured by notched Izod at similar Flexural modulus than the comparative runs.

This is further illustrated for all the data by plotting the notched Izod versus the Flexural Modulus for each the comparative examples relative to the inventive examples. As the plot below illustrates the inventive examples have a higher impact property (notched Izod) at equivalent Flexural Modulus.

The improved impact strength at comparable modulus results from a higher molecular weight, as measured by IV, of Component B. The higher the molecular weight of component B, the better the impact test values.

The known metallocenes comparison 1 and 2 are limited to low values for this molecular weight as measured by the IV of Component B. The maximum value of IV for the comparative metallocenes was a value of about 1.7 for run 9 (Table 1B) with the ethylene/propylene at a 4.2/0.8 ratio. Inventive metallocene B at this ratio produced an IV that ranged from 1.99 in run 13 to 2.338 in run 18. The inventive metallocene D produced an ICP with an IV of 3.508 in run 40. In fact, for all runs with inventive metallocene D the IV values were greater than 2.2 for all ICP products and ranged from 2.202 (run 39) to 3.667 (run 38). These high IV values will result in further improved impact properties.

TABLE 1A

| RUN # | Supported Metallocene Catalyst System | Cat Amount (mg) | Yield (g) | Efficiency (Kg/g cat) | H2 (mmol) | Time split (min.) | $C_2^-/C_3^-$ flow rates (l/min.) |
|---|---|---|---|---|---|---|---|
| 1 | E | 31 | 243.9 | 7.87 | 78 | 60/150 | 4.1/0.9 |
| 2 | E | 30 | 155.1 | 5.17 | 78 | 60 | |
| 3 | COMP. 1 | 31 | 198.9 | 6.42 | 78 | 60 | |
| 4 | COMP. 1 | 30 | 224.8 | 7.49 | 78 | 60/90 | 4.1/0.9 |
| 5 | A | 59 | 226.1 | 3.83 | 47 | 60/120 | 4.2/0.8 |
| 6 | A | 59 | 212.8 | 3.61 | 47 | 60/120 | 4.4/0.6 |
| 7 | A | 59 | 191.1 | 3.24 | 47 | 60 | |
| 8 | A | 60 | 215.6 | 3.59 | 47 | 60/120 | 4.7/0.3 |
| 9 | COMP. 2 | 60 | 272.6 | 4.54 | 54 | 60/120 | 4.2/0.8 |
| 10 | COMP. 2 | 61 | 196.9 | 3.23 | 54 | 60 | |
| 11 | A | 61 | 141.8 | 2.32 | 47 | 60/120 | 4.4/0.6 |
| 12 | A | 60 | 192.4 | 3.21 | 47 | 60/120 | 4.7/0.3 |
| 13 | B | 63 | 80.0 | 1.27 | 23 | 60/120 | 4.2/0.8 |
| 14 | B | 63 | 97.8 | 1.55 | 23 | 60/120 | 4.4/0.6 |
| 15 | B | 60 | 72.2 | 1.20 | 23 | 60 | |
| 16 | B | 61 | 82.2 | 1.35 | 23 | 60/120 | 4.0/1.0 |
| 17 | B | 60 | 89.0 | 1.48 | 23 | 60/120 | 4.1/0.9 |
| 18 | B | 150 | 180.2 | 1.20 | 23 | 30/120 | 4.2/0.8 |
| 19 | B | 152 | 153.8 | 1.01 | 23 | 30/120 | 4.0/1.0 |

TABLE 1A-continued

| RUN # | Supported Metallocene Catalyst System | Cat Amount (mg) | Yield (g) | Efficiency (Kg/g cat) | H2 (mmol) | Time split (min.) | $C_2^-/C_3^-$ flow rates (l/min.) |
|---|---|---|---|---|---|---|---|
| 20 | B | 151 | 87.4 | 0.58 | 23 | 30 | |
| 21 | E | 43 | 139.0 | 3.23 | 62 | 60 | |
| 22 | E | 44 | 154.0 | 3.50 | 62 | 60/150 | 4.1/0.9 |
| 23 | E | 43 | 102.2 | 2.38 | 62 | 60/150 | 3.6/1.4 |
| 24 | E | 43 | 81.1 | 1.89 | 78 | 60/150 | 4.0/1.0 |
| 25 | E | 41 | 53.3 | 1.30 | 78 | 60 | |

TABLE 1B

| RUN # | Total Ethylene (wt %) | Ethylene in Comp. B (wt %) | Total Comp. B (wt %) | Final MFR (dg/10 min.) | Melting Point (° C.) | MW | MWD | Comp. B IV |
|---|---|---|---|---|---|---|---|---|
| 1 | 10.24 | 50.80 | 20.16 | 114.0 | 151.1 | 103.5 | 2.88 | 0.9786 |
| 2 | | | | 459.2 | 150.2 | 75.4 | 3.15 | |
| 3 | | | | 58.95 | 150.9 | 135.7 | 3.15 | |
| 4 | 7.82 | 50.04 | 15.63 | 127.16 | 150.0 | 100.4 | 3.11 | 0.708 |
| 5 | 3.87 | 47.36 | 8.17 | 490 | 149.6 | 116.5 | 4.18 | 1.637 |
| 6 | 5.93 | 51.70 | 11.5 | 118 | 149.8 | 148.7 | 4.74 | 2.36 2.46 |
| 7 | | | | 123 | 148.6 | 73.5 | 2.78 | |
| 8 | 8.13 | 58.96 | 13.8 | 74.2 | 150.3 | 160.0 | 4.98 | 2.221 2.199 |
| 9 | 9.74 | 51.52 | 18.91 | 4.98 | 151.0 | 210.4 | 2.96 | 1.7127 |
| 10 | | | | 3.12 | 151.0 | 278.0 | 2.49 | |
| 11 | 5.23 | 55.72 | 9.39 | 129.0 | 150.4 | 147.4 | 4.25 | 2.18 |
| 12 | 12.08 | 63.62 | 18.99 | 10.02 | 150.3 | 1,139.0 | 456 | 1.55 |
| 13 | 6.19 | 47.44 | 13.05 | 21.1 | 154.97 | 168.6 | 2.84 | 1.99 |
| 14 | 8.81 | 54.69 | 16.11 | 19.9 | 155.3 | 169.7 | 3.00 | 2.37 |
| 15 | | | | 72.84 | 156.57 | 158.2 | 2.77 | |
| 16 | 4.12 | 40.33 | 10.22 | 53.03 | 154.7 | 148.1 | 2.74 | 1.585 |
| 17 | 3.59 | 45.88 | 7.82 | 51.27 | 154.2 | 145.2 | 2.79 | 1.351 |
| 18 | 11.10 | 49.56 | 22.40 | 15.47 | 155.5 | 192.8 | 3.09 | 2.338 |
| 19 | 8.80 | 43.02 | 20.46 | 16.95 | 155.3 | 194.1 | 3.47 | 1.742 |
| 20 | | | | 30.26 | 154.63 | 106.6 | 2.27 | |
| 21 | | | | 10.3 | 151.83, minor 138.33 | 225.6 | 1.93 | |
| 22 | 10.95 | 50.37 | 21.74 | 3.66 | 151.97 | 302.3 | 2.78 | 2.185 |
| 23 | 6.46 | 36.4 | 17.75 | 7.01 | 152.77 | 240.3 | 2.44 | 2.11 |
| 24 | 9.37 | 47.34 | 19.79 | 131.01 | 150.83 | 122.6 | 4.26 | 2.063 |
| 25 | | | | 681.8 | 151.23 | 76.9 | 3.5 | |

TABLE 2A

| RUN # | Supported Metallocene Catalyst System | Cat Amount (mg) | Yield (g) | Efficiency (Kg/g cat) | H2 (mmol) | Time split (min.) | $C_2^-/C_3^-$ flow rates (l/min.) |
|---|---|---|---|---|---|---|---|
| 26 | C | 61 | 158.2 | 2.59 | 47 | 60/120 | 4.0/1.0 |
| 27 | C | 60 | 139.9 | 2.33 | 47 | 60 | |
| 28 | C | 61 | 168.9 | 2.77 | 47 | 60/120 | 4.4/0.6 |
| 29 | C | 60 | 42.3 | 0.71 | 16 | 60 | |
| 30 | C | 61 | 94.7 | 1.55 | 31 | 60 | |
| 31 | C | 300 | 159.8 | 0.53 | 7.8 | 60 | |
| 32 | C | 300 | 51.4 | 0.17 | 7.8 | 21 | |
| 33 | C | 300 | 276.2 | 0.92 | 7.8 | 64/180 | 4.0/1.0 |
| 34 | D | 121 | 63.0 | 0.52 | 7.8 | 60 | |
| 35 | D | 120 | 79.4 | 0.66 | 7.8 | 60/90 | 4.0/1.0 |
| 36 | D | 122 | 99.1 | 0.81 | 7.8 | 60/90 | 4.1/0.9 |
| 37 | D | 123 | 71.2 | 0.58 | 7.8 | 60/90 | 3.6/1.4 |
| 38 | D | 120 | 95.2 | 0.79 | 7.8 | 60/120 | 4.0/1.0 |
| 39 | D | 121 | 143.7 | 1.19 | 16 | 60/90 | 4.0/1.0 |
| 40 | D | 124 | 167.6 | 1.35 | 16 | 60/90 | 4.2/0.8 |
| 41 | D | 120 | 101.5 | 0.85 | 16 | 60 | |
| 42 | D | 121 | 121.2 | 1.00 | 16 | 60/90 | 4.4/0.6 |

TABLE 2B

| RUN # | Total Ethylene (wt %) | Ethylene in Comp. B (wt %) | Total Comp. B (wt %) | Final MFR (dg/10 min.) | Melting Point (° C.) | MW | MWD | IV of Comp. B |
|---|---|---|---|---|---|---|---|---|
| 26 | 3.584 | 43.25 | | 971.02 | 152.17 | 75.6 | 2.50 | 1.121 |
| 27 | | | | 1013.8 | 152.1 (157.17 minor) | 70.9 | 2.27 | |
| 28 | 4.62 | 57.52 | | 954.7 | 151.57 | 69.2 | 2.39 | 2.083 |
| 29 | | | | 142.5 | 152.91 | 120.1 | 2.38 | |
| 30 | | | | 420.7 | 152.1 | 91.7 | 2.19 | |
| 31 | | | | 129.85 | 153.23 | 127.3 | 3.62 | |
| 32 | | | | 268.69 | 152.97 | 108.1 | 4.41 | |
| 33 | 15.07, 14.24 | 48.96, 47.85 | | 11.94 | 154.1 | 238.1 | 14.49 | 1.993 |
| 34 | | | | 76.55 | 151.83 | 138.5 | 2.20 | |
| 35 | 8.199 | 39.92 | | 14.16 | 153.43 | 213.6 | 3.05 | 2.833 |
| 36 | 7.068 | 42.81 | | 15.43 | 152.03 | 196.3 | 3.01 | 2.505 |
| 37 | 8.294 | 26.52 | | 4.92 | 152.77 | 248.0 | 3.28 | 2.662 |
| 38 | 15.85 | 39.17 | | 0.479 | 153.23 | 306.7 | 4.14 | 3.667 |
| 39 | 7.521 | 37.72 | | 27.72 | 153.03 | 204.7 | 3.61 | 2.202 |
| 40 | 10.02 | 44.73 | | 5.8 | 152.63 | 235.8 | 3.58 | 3.508 |
| 41 | | | | 75.86 | 151.03 | 135.8 | 2.30 | |
| 42 | 21.21 | 56.17 | | 0.53 | 152.10 | 280.9 | 3.84 | |

TABLE 3

| APPL. RUN # | Description | Supported Metallocene Catalyst System | MFR (dg/10 min) | % Xylene Sol (wt %) | % Xylene Insol (wt %) | FTIR data Total C2 (wt %) | C2 in Comp. B (wt %) | Total Comp. B (wt %) |
|---|---|---|---|---|---|---|---|---|
| 5 | ICP | A | 490 | 6.6 | 93.8 | 3.87 | 47.36 | 8.2 |
| 6 | ICP | A | 118 | 6.8 | 93.2 | 5.93 | 51.7 | 11.5 |
| 7 | Homo PP | A | 123 | 1 | 98.8 | | | |
| 8 | ICP | A | 74.2 | 5.4 | 94.5 | 8.13 | 58.96 | 13.8 |
| 11 | ICP | A | 129.0 | 6.7 | 93.5 | 5.23 | 55.72 | 9.5 |
| 12 | ICP | A | 10.02 | 4.3 | 95.9 | 12.08 | 63.62 | 19 |
| 13 | ICP | B | 21.1 | 13.3 | 86.7 | 6.19 | 47.44 | 13 |
| 14 | ICP | B | 19.9 | 14.3 | 85.7 | 8.81 | 54.69 | 16.1 |
| 15 | Homo PP | B | 72.84 | 1.1 | 99 | | | |
| 16 | ICP | B | 53.03 | 11.7 | 88.5 | 4.12 | 40.33 | 10.2 |
| 17 | ICP | B | 51.27 | 8.4 | 91.6 | 3.59 | 45.88 | 7.8 |
| 18 | ICP | B | 15.47 | 19.2 | 80.4 | 11.1 | 49.56 | 22.4 |
| 19 | ICP | B | 16.95 | 20.9 | 79.2 | 8.8 | 43.02 | 20.5 |
| 20 | Homo PP | B | 30.26 | 1.1 | 98.9 | | | |

TABLE 4

| APPL RUN # | Description | Supported Metallocene Catalyst System | MFR (dg/10 min) | % Xylene Sol (wt %) | % Xylene Insol (wt %) | FTIR data Total C2 (wt %) | C2 in Comp. B (wt %) | Total Comp. B (wt %) | IV Of Comp. B |
|---|---|---|---|---|---|---|---|---|---|
| 1 | ICP | E | 114.0 | 25.6 | 74.5 | 10.24 | 50.8 | 20.2 | 0.979 |
| 2 | Homo PP | E | 459.2 | 1.2 | 98.8 | | | | |
| 3 | Homo PP | Comp. 1 | 58.95 | 0.6 | 99.4 | | | | |
| 4 | ICP | Comp. 1 | 127.16 | 20.4 | 79.7 | 7.82 | 50.04 | 15.6 | 0.708 |
| 9 | ICP | Comp. 2 | 4.98 | 23.5 | 76.2 | 9.74 | 51.52 | 18.9 | 1.713 |
| 10 | Homo PP | Comp. 2 | 3.12 | 0.9 | 99.1 | | | | |
| 13 | ICP | B | 129.0 | 12.4 | 86.9 | | | | |
| 21 | Homo PP | E | 10.3 | 0.7 | 99.3 | | | | |
| 22 | ICP | E | 3.66 | 24 | 75.6 | 10.95 | 50.37 | 21.7 | 2.185 |
| 23 | ICP | E | 7.01 | 20.9 | 79.3 | 6.46 | 36.4 | 17.7 | 2.11 |
| 24 | ICP | E | 131.01 | 22 | 78.1 | 9.37 | 47.34 | 19.8 | 2.06 |
| 25 | Homo PP | E | 681.8 | 2.1 | 98 | | | | |

TABLE 5

| APPL RUN # | Description | Supported Metallocene Cat. Syst. | MFR (dg/10 min) | Xylene Solubles ('low' MW peak) | | | | Xylene Solubles ('high' MW peak) | | | | Xylene Insolubles | | | |
|---|---|---|---|---|---|---|---|---|---|---|---|---|---|---|---|
| | | | | Mn | Mw | Mz | Mw/Mn | Mn | Mw | Mz | Mw/Mn | Mn | Mw | Mz | Mw/Mn |
| 1 | ICP | E | 114.0 | 1251 | 1554 | 1874 | 1.24 | 38015 | 74567 | 115589 | 1.96 | 12314 | 32426 | 54966 | 2.63 |
| 2 | Homo PP | E | 459.2 | 1513 | 2013 | 2599 | 1.33 | 18384 | 30191 | 45639 | 1.64 | 17552 | 41149 | 67038 | 2.34 |
| 3 | Homo PP | Comp. 1 | 58.95 | 1441 | 1952 | 2630 | 1.35 | 14448 | 22536 | 35314 | 1.56 | 30510 | 63658 | 97817 | 2.09 |
| 4 | ICP | Comp. 1 | 127.16 | 981 | 1062 | 1140 | 1.08 | 15647 | 33205 | 51601 | 2.12 | 16342 | 42791 | 71409 | 2.62 |
| 9 | ICP | Comp. 2 | 4.98 | 987 | 1180 | 1433 | 1.2 | 48475 | 118629 | 214628 | 2.45 | 41276 | 106195 | 179010 | 2.57 |
| 10 | Homo PP | Comp. 2 | 3.12 | 1071 | 1376 | 1834 | 1.29 | 15113 | 30638 | 56220 | 2.03 | 61668 | 142260 | 249807 | 2.31 |
| 13 | ICP | B | 21.1 | 941 | 1099 | 1308 | 1.17 | 44501 | 187149 | 515199 | 4.21 | 69282 | 167811 | 342963 | 2.42 |
| 21 | Homo PP | E | 10.3 | 1114 | 1383 | 1715 | 1.24 | 12228 | 23656 | 42278 | 1.93 | 82347 | 184675 | 309914 | 2.24 |
| 22 | ICP | E | 3.66 | 929 | 1153 | 1502 | 1.24 | 77378 | 211251 | 413832 | 2.73 | 97431 | 248553 | 471070 | 2.55 |
| 23 | ICP | E | 7.01 | 982 | 1165 | 1403 | 1.19 | 57316 | 166144 | 312133 | 2.9 | 85158 | 206876 | 354334 | 2.43 |
| 24 | ICP | E | 131.01 | 1515 | 2556 | 4282 | 1.69 | 74803 | 161031 | 319874 | 2.15 | 27750 | 76477 | 129002 | 2.76 |
| 25 | Homo PP | E | 681.8 | 1430 | 1868 | 2472 | 1.31 | 10530 | 13500 | 17834 | 1.28 | 24398 | 76119 | 137103 | 3.12 |

TABLE 6

| APPL RUN # | Description | Supported Metallocene Cat. Syst. | MFR dg/10 min | Xylene Solubles ('low' MW peak) | | | | Xylene Solubles ('high' MW peak) | | | | Xylene Insolubles | | | |
|---|---|---|---|---|---|---|---|---|---|---|---|---|---|---|---|
| | | | | Mn | Mw | Mz | Mw/Mn | Mn | Mw | Mz | Mw/Mn | Mn | Mw | Mz | Mw/Mn |
| 5 | ICP | A | 490 | 713 | 740 | 772 | 1.04 | 46485 | 196796 | 608279 | 4.23 | 36452 | 117941 | 384107 | 3.24 |
| 6 | ICP | A | 118 | 721 | 751 | 786 | 1.04 | 32808 | 173994 | 652286 | 5.3 | 38405 | 150533 | 577951 | 3.92 |
| 7 | Homo PP | A | 123 | 746 | 775 | 805 | 1.04 | 2224 | 3418 | 6092 | 1.54 | 31525 | 77176 | 139014 | 2.45 |
| 8 | ICP | A | 74.2 | 714 | 743 | 776 | 1.04 | 36731 | 157042 | 553553 | 4.28 | 37994 | 133529 | 493184 | 3.51 |
| 11 | ICP | A | 129.0 | 712 | 741 | 774 | 1.04 | 39823 | 188272 | 544445 | 4.73 | 39618 | 147046 | 523576 | 3.71 |
| 12 | ICP | A | 10.02 | 739 | 774 | 814 | 1.05 | 22407 | 91802 | 367841 | 4.1 | 49352 | 214835 | 834003 | 4.35 |
| 13 | ICP | B | 21.1 | 741 | 775 | 814 | 1.05 | 32783 | 134448 | 347619 | 4.1 | 73240 | 168231 | 330135 | 2.3 |
| 14 | ICP | B | 19.9 | 774 | 822 | 884 | 1.06 | 76080 | 247012 | 646524 | 3.25 | 48027 | 140429 | 300877 | 2.92 |
| 15 | Homo PP | B | 72.84 | 720 | 756 | 800 | 1.05 | 11124 | 16144 | 23634 | 1.45 | 65242 | 150447 | 276068 | 2.31 |
| 16 | ICP | B | 53.03 | 735 | 765 | 803 | 1.04 | 26643 | 128696 | 380989 | 4.83 | 67746 | 158765 | 317323 | 2.34 |
| 17 | ICP | B | 51.27 | 733 | 759 | 790 | 1.04 | 40054 | 99847 | 204429 | 2.49 | 37641 | 130382 | 468779 | 3.46 |
| 18 | ICP | B | 15.47 | 721 | 741 | 764 | 1.03 | 61128 | 250368 | 694151 | 4.1 | 50670 | 134806 | 284392 | 2.66 |
| 19 | ICP | B | 16.95 | 710 | 726 | 744 | 1.02 | 71050 | 246743 | 632260 | 3.47 | 53550 | 131611 | 251500 | 2.46 |
| 20 | Homo PP | B | 30.26 | 857 | 1043 | 1371 | 1.22 | 9567 | 16302 | 25965 | 1.7 | 75064 | 161464 | 317578 | 2.15 |

TABLE 7A

| Run # | Supported Metallocene Cat. System | TEAL Amount (mls) | Cat Amount (mg) | Yield (g) | Efficiency (Kg/g cat) | H2 (delta psi) | Time split (min.) | $C_2^=/C_3^=$ flow rates (l/min.) |
|---|---|---|---|---|---|---|---|---|
| 43 | F | 0.3 | 123 | 261.1 | 2.12 | 697.5 | 60/90 | 4.0/1.0 |
| 44 | F | 0.3 | 120 | 289.8 | 2.42 | 542.5 | 60/90 | 4.0/1.0 |
| 45 | Comp 3 | 0.3 | 60 | 219.6 | 3.66 | 930.0 | 60/75 | 4.8/1.2 |
| 46 | Comp 3 | 0.3 | 64 | 220.0 | 3.44 | 930.0 | 60/75 | 2.0/0.5 |
| 47 | Comp 4 | 0.3 | 61 | 275.9 | 4.52 | 1007.5 | 35/45 | 4.8/1.2 |
| 48 | Comp 4 | 0.3 | 61 | 278.4 | 4.56 | 1007.5 | 35/45 | 2.0/0.5 |
| 49 | G | 0.3 | 124 | 246.3 | 1.99 | 542.5 | 60/90 | 4.0/1.0 |
| 50 | G | 0.3 | 122 | 269.5 | 2.21 | 542.5 | 60/90 | 4.0/1.0 |

TABLE 7B

| RUN # | Total Ethylene (wt %) | Ethylene In Rubber (wt %) | Total Rubber (wt %) | Final MFR (g/10 min.) | Melting Point (° C.) | IV of Copolymer |
|---|---|---|---|---|---|---|
| 43 | 6.34 | 43.23 | 14.7 | 206 | 147.98 | 1.678 |
| 44 | 2.07 | 40.89 | 5.1 | 671 | 148.05 | |

TABLE 7B-continued

| RUN # | Total Ethylene (wt %) | Ethylene In Rubber (wt %) | Total Rubber (wt %) | Final MFR (g/10 min.) | Melting Point (° C.) | IV of Copolymer |
|---|---|---|---|---|---|---|
| 45 | 12.66 | 50.85 | 24.9 | 27.0 | 149.69 | 0.789 |
| 46 | 8.60 | 47.40 | 18.1 | 33.2 | 149.04 | 0.651 |
| 47 | 11.48 | 53.03 | 21.6 | 18.2 | 151.61 | 0.637 |
| 48 | 7.61 | 49.49 | 15.4 | 44.6 | 151.69 | 0.786 |
| 49 | 7.09 | 44.46 | 15.9 | 69.2 | 147.55 | 1.618 |
| 50 | 5.15 | 43.51 | 11.8 | 132 | 147.34 | 1.619 |

TABLE 8

| Application Run Number | Supported Metallocene Catalyst System | MFR (dg/min) | HDT (° C.) | FLEX MOD (psi) | Notched IZOD (23° C.) (ft.lb./in.) |
|---|---|---|---|---|---|
| 43 | F | 206 | 95.8 | 151846 | 1.57 |
| 44 | F | 671 | 114.9 | 211749 | 0.42 |
| 46* | Comp. 3 | 33.2 | 81 | 97490 | 1.86 |
|  |  |  | 98 | 158627 | 1.25 |
| 47* | Comp. 4 | 18.2 | 87 | 124709 | 1.4 |
|  |  |  | 107 | 155790 | 0.81 |
| 48* | Comp. 4 | 44.6 | 76 | 91609 | 1.51 |
|  |  |  | 102 | 155702 | 0.74 |
| 49 | G | 69.2 | 95 | 136745 | 2.37 |
| 50 | G | 132 | 97.5 | 158309 | 1.7 |

*Two impact/modulus tests were carried out because of differences in visual appearance of the samples from these runs.

What is claimed is:

1. A propylene impact copolymer composition comprising:
   (a) from about 40% to about 95% by weight Component A based on the total weight of the impact copolymer, Component A comprising propylene homopolymer or copolymer, wherein the copolymer comprises 10% or less by weight ethylene, butene, hexene or octene comonomer and the amount of amorphous polypropylene in Component A is less than 2 wt %;
   (b) from about 5% to about 60% by weight Component B based on the total weight of the impact copolymer, Component B comprising propylene copolymer, wherein the copolymer comprises from about 20% to about 70% by weight ethylene, butene, hexene and/or octene comonomer, and from about 80% to about 30% by weight propylene.

2. The composition of claim 1, wherein Component A is a propylene homopolymer.

3. The composition of claim 1, wherein Component B consist essentially of propylene and from about 20% to about 70% by weight ethylene.

4. The composition of claim 1, wherein Component B consists essentially of propylene and from about 30% to about 65% by weight ethylene.

5. The composition of claim 1, wherein Component B has a molecular weight distribution of less than 3.0.

6. The composition of claim 1, wherein Component B has a weight average molecular weight of at least 100,000.

7. The composition of claim 1, wherein Component A has a weight average molecular weight of at least 100,000.

8. The composition of claim 1, wherein Component B has a weight average molecular weight of at least 200,000.

9. The composition of claim 1, wherein the amount of amorphous polypropylene in Component A is less than 1 wt %.

10. The composition of claim 1, wherein Component B has an intrinsic viscosity of greater than 1.00 dl/g.

11. The composition of claim 1, wherein Component B has an intrinsic viscosity of greater than 2.00 dl/g.

12. The composition of claim 1, wherein Component B has less than 10% by weight of a crystalline portion.

13. The composition of claim 12, wherein the comonomer content in the crystalline portion is the same as in the remainder of Component B.

14. The composition of claim 1, wherein the propylene impact copolymer is prepared in a two-stage polymerization process using a metallocene catalyst system comprising a metallocene selected from the group consisting of: rac-dimethylsiladiyl(2-iPr-4-phenylindenyl)$_2$zirconium dichloride; rac-dimethylsiladiyl(2-iPr-4-[1-naphthyl]indenyl)$_2$zirconium dichloride; rac-dimethylsiladiyl(2-iPr-4-[3,5-dimethylphenyl]indenyl)$_2$zirconium dichloride; rac-dimethylsiladiyl(2-iPr-4-[2-methyl-phenyl]indenyl)$_2$zirconium dichloride; and rac-dephenylsiladiyl(2-methyl-4-[1-naphthyl]indenyl)$_2$zirconium dichloride.

* * * * *